United States Patent
Mistretta

(10) Patent No.: US 8,620,404 B2
(45) Date of Patent: Dec. 31, 2013

(54) SYSTEM AND METHOD OF HIGH-FRAME RATE, TIME-RESOLVED, THREE-DIMENSIONAL MAGNETIC RESONANCE ANGIOGRAPY

(75) Inventor: Charles A. Mistretta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 330 days.

(21) Appl. No.: 13/191,388

(22) Filed: Jul. 26, 2011

(65) Prior Publication Data
US 2013/0030279 A1    Jan. 31, 2013

(51) Int. Cl.
A61B 5/055    (2006.01)

(52) U.S. Cl.
USPC .......................................... 600/410; 382/128

(58) Field of Classification Search
None
See application file for complete search history.

(56) References Cited

U.S. PATENT DOCUMENTS

| | | | |
|---|---|---|---|
| 5,502,385 A | 3/1996 | Kuhn et al. | |
| 5,603,322 A | 2/1997 | Jesmanowicz et al. | |
| 5,604,778 A | 2/1997 | Polacin et al. | |
| 5,933,006 A | 8/1999 | Rasche et al. | |
| 6,324,245 B1 | 11/2001 | Tam | |
| 6,487,435 B2 | 11/2002 | Mistretta et al. | |
| 6,490,472 B1 | 12/2002 | Li et al. | |
| 6,710,686 B2 | 3/2004 | Mertelmeier et al. | |
| 6,807,248 B2 | 10/2004 | Mihara et al. | |
| 6,954,067 B2 | 10/2005 | Mistretta | |
| 7,519,412 B2 | 4/2009 | Mistretta | |
| 7,917,189 B2 | 3/2011 | Mistretta | |
| 2008/0219535 A1 | 9/2008 | Mistretta et al. | |
| 2009/0076369 A1 | 3/2009 | Mistretta | |
| 2010/0286504 A1 | 11/2010 | Mistretta et al. | |
| 2011/0037761 A1 | 2/2011 | Mistretta et al. | |
| 2011/0038517 A1 | 2/2011 | Mistretta et al. | |

FOREIGN PATENT DOCUMENTS

| | | |
|---|---|---|
| EP | 0627633 A1 | 12/1994 |
| JP | 11299769 A | 11/1999 |
| WO | 2005026765 A1 | 3/2005 |
| WO | 2005069031 A1 | 7/2005 |

OTHER PUBLICATIONS

Aggarwal, et al., Imaging in Turbid Media by Modified Filtered Back Projection method Using Data from Monte Carlo Simulation, Proc. of SPIE, 2003, 5047:314-324.

Badea, et al., Experiments with the Nonlinear and Chaotic Behaviour of the Multiplicative Algebraic Reconstruction Technique (MART) Algorithm for Computed Tomography, Phys. Med. Biol., 2004, 49:1455-1474.

(Continued)

*Primary Examiner* — Long V. Le
*Assistant Examiner* — Bradley Impink
(74) *Attorney, Agent, or Firm* — Quarles & Brady, LLP

(57) ABSTRACT

A system and method for generating time-resolved 3D medical images of a subject includes acquiring a time series of two-dimensional (2D) data sets from a portion of the subject using a magnetic resonance imaging (MRI) system and reconstructing the time series of 2D data sets into a 2D time series of images of the subject having a given frame rate. The process also includes acquiring a time-independent, 3D volume of the portion of the subject and combining the 2D time series of images of the subject with the time-independent 3D volume of the subject to generate a set of time-dependent 3D volume images of the portion of the subject at the given frame rate.

19 Claims, 4 Drawing Sheets

(56) References Cited

OTHER PUBLICATIONS

Baltes, et al., Considerations on Training Data in k-t BLAST / k-t SENSE Accelerated Quantitative Flow Measurements, Proc. Intl. Soc. Mag. Reson. Med., 2005, 13:383.

Barger, et al., Single Breath-Hold 3D Contrast-Enhanced Method for Assessment of Cardiac Function, Mag. Reson. Med., 2000, 44:821-824.

Boubertakh, et al., Dynamic Images Reconstruction Using kt-BLAST Without Training Data, Proc. Intl. Soc. Mag. Reson. Med., 2004, 11:343.

Cashen, et al., Comparison of Temporal and Spatial Undersampling Techniques for Time-Resolved Contrast-Enhanced MR Angiography, Proc. Intl. Soc. Mag. Reson. Med., 2005, 13:380.

Du, et al., Time-Resolved, Undersampled Projection Reconstruction Imaging for High-Resolution CE-MRA of the Distal Runoff Vessels, Mag. Reson. Med., 2002, 48:516-522.

Fahrig, et al., Use of a C-Arm System to Generate True Three-Dimensional Computed Rotational Angiograms: Preliminary In Vitro and In Vivo Results, Am. J. Neuroradiol., 1997, 18:1507-1514.

Garden, et al., 3-D Reconstruction of the Heart from Few Projections: A Practical Implementation of the McKinnon-Bates Algorithm, IEEE Transactions on Medical Imaging, 1986, MI-5(4):233-239.

Golay, et al., Presto-Sense: An Ultrafast Whole-Brain fMRI Technique, Mag. Reson. Med., 2000, 43:779-786.

Hansen, et al., On the Influence of Training Data Quality in k-t BLAST Reconstruction, Mag. Reson. Med., 2004, 52:1175-1183.

Hansen, et al., A Study of the Spatial-Temporal Tradeoff in k-t BLAST Reconstruction, Proc. Intl. Soc. Mag. Reson. Med., 2004, 11:536.

Hansen, et al., k-t BLAST Reconstruction from Arbitrary k-t Space Sampling: Application to Dynamic Radial Imaging, Proc. Intl. Soc. Mag. Reson. Med., 2005, 13:684.

Hansen, et al., k-t BLAST Reconstruction from Non-Cartesian k-t Space Sampling, Mag. Reson. Med., 2006, 55:85-91.

Huang, et al., Reconstruction with Prior Information for Dynamic MRI, Proc. Intl. Soc. Mag. Reson. Med., 2004, 11:2680.

Huang, et al., Time-Resolved 3D MR Angiography by Interleaved Biplane Projections, Proc. Intl. Soc. Mag. Reson. Med., 2005, 13:1707.

Irarrazaval, et al., Reconstruction of Undersampled Dynamic Images Based on Time Frame Registration, Proc. Intl. Soc. Mag. Reson. Med., 2004, 11:342.

Johnson, et al., Average and Time-Resolved Dual Velocity Encoded Phase Contrast Vastly Undersampled Isotropic Projection Imaging, Med. Phys. Univ. of WI, Madison WI.

Johnson, et al., Transtenotic Pressure Gradient Measurements Using Phase Contrast Vastly Undersampled Projection Imaging (PC-VIPR) in a Canine Model, Med. Phys. Univ. of WI, Madison, WI.

Koladia, et al., Rapid 3D PC-MRA Using Spiral Projection Imaging, Proc. Intl. Soc. Mag. Reson. Med., 2005, 13:2403.

Krishnan, et al., Spatio-Temporal Bandwidth-Based Acquisition for Dynamic Contrast-Enhanced Magnetic Resonance Imaging, J. Magn. Reson. Imaging, 2004, 20:129-137.

Launay, et al., 3D Reconstruction of Cerebral Vessels and Pathologies from a Few Biplane Digital Angiographies, Lecture Notes in Computer Science, 1996, 1131/1996:123-128.

Lauterbur, et al., Magnetic Resonance Imaging with a Priori Constraints: Possibilities and Limitations, 18th Annual International Conference of the IEEE Engineering in Medicine and Biology Society, Amsterdam 1996, pp. 2170-2171.

Liang, et al., Constrained Reconstruction Methods in MR Imaging, Reviews of Mag. Reson. Med., 1992, 4:67-185.

Liang, et al., Constrained Imaging, Overcoming the Limitations of the Fourier Series, IEEE Engineering in Medicine and Biology, 1996, pp. 126-132.

Liang, et al., Fast Algorithms for GS-Model-Based Image Reconstruction in Data-Sharing Fourier Imaging, IEEE Transactions on Medical Imaging, 2003, 22(8):1026-1030.

Lustig, et al., k-t SPARSE: High Frame Rate Dynamic MRI Exploiting Spatio-Temporal Sparsity, Proc. Intl. Soc. Mag. Reson. Med., 2006, 14, 1 page.

Lustig, et al., Rapid MR Imaging with 'Compressed Sensing' and Randomly Under-Sampled 3DFT Trajectories, Proc. Intl. Soc. Mag. Reson. Med., 2006, 14, 1 page.

Madore, et al., New Approach to 3D Time-Resolved Angiography, Mag. Reson. Med., 2002, 47:1022-1025.

Mc Kinnon, et al., Towards Imaging the Beating Heart Usefully with a Conventional CT Scanner, IEEE Transactions on Biomedical Engineering, 1981, BME-28(2):123-127.

Mistretta, et al., Highly Constrained Backprojection for Time-Resolved MRI, Mag. Reson. Med., 2006, 55:30-40.

Mitsouras, et al., Accelerated MR Imaging Via FOLDing the non-Fourier Encoded Dimensions, Proc. Intl. Soc. Mag. Reson. Med., 2004, 11:2092.

Nowinski, The Iterated Normalized Backprojection Method of Image Reconstruction, Institute of Computer Science, Polish Academy of Sciences, Ordona 21, 01-237 Warsaw, Poland.

Pipe, et al., Spiral Projection Imaging: A New Fast 3D Trajectory, Proc. Intl. Soc. Mag. Reson. Med., 2005, 13:2402.

Price, et al., Practical Aspects of Functional MRI (NMR Task Group #8), Med. Phys., 2002, 29(8):1892-1912.

Pruessmann, et al., Advances in Sensitivity Encoding With Arbitrary k-Space Trajectories, Mag. Reson. Med., 2001, 46:638-651.

Schmidlin, et al., Subsets and Overrelaxation in Iterative Image Reconstruction, Phys. Med. Biol., 1999, 44:1385-1396.

Tsao, et al., Unifying Linear Prior-Information-Driven Methods for Accelerated Image Acquisition, Mag. Reson. Med., 2001, 46:652-660.

Tsao, et al., k-t BLAST and k-t SENSE: Dynamic MRI With High Frame Rate Exploiting Spatiotemporal Correlations, Mag. Reson. Med., 2003, 50:1031-1042.

Tsao, et al., Optimized Canonical Sampling Patterns in k-t Space with Two and Three Spatial Dimensions for k-t BLAST and k-t, Proc. Intl. Soc. Mag. Reson. Med., 2004, 11:261.

Tsao, et al., Moving-Buffer k-t BLAST for Real-Time Reconstruction: Cartesian & Simplified Radial Cases, Proc. Intl. Soc. Mag. Reson. Med., 2004, 11:635.

Tsao, et al., Optimizing Spatiotemporal Sampling for k-t BLAST and k-t SENSE: Application to High-Resolution Real-Time Cardiac Steady-State Free Precession, Mag. Reson. Med., 2005, 53:1372-1382.

Webb, et al., Applications of Reduced-Encoding MR Imaging with Generalized-Series Reconstruction (RIGR), JMRI, 1993, 3:925-928.

Wentland, et al., Technique for Acquiring MR Images of CSF Flow During a Valsalva Maneuver, Med. Phys. Univ. of WI, Madison WI.

Xiang, et al., K-Space Description for MR Imaging of Dynamic Objects, MRM, 1993, 29:422-428.

United States Patent and Trademark Office, Office Action Summary and Detailed Action, U.S. Appl. No. 11/482,372, Jun. 27, 2007.

Applicant, Amendment (Response to Jun. 27, 2007 Office Action), U.S. Appl. No. 11/482,372, filed Jul. 27, 2007.

United States Patent and Trademark Office, Office Action Summary and Detailed Action, U.S. Appl. No. 11/482,372, Aug. 22, 2007.

Applicant, Amendment (Response to Aug. 22, 2007 Office Action), U.S. Appl. No. 11/482,372, filed Nov. 2, 2007.

United States Patent and Trademark Office, Office Action Summary and Detailed Action, U.S. Appl. No. 11/482,372, Jan. 25, 2008.

Applicant, Amendment (Response to Jan. 25, 2008 Office Action), U.S. Appl. No. 11/482,372, filed Mar. 21, 2008.

United States Patent and Trademark Office, Office Action Summary and Detailed Action, U.S. Appl. No. 11/482,372, Jun. 25, 2008.

Applicant, Response to Final Office Action, U.S. Appl. No. 11/482,372, Aug. 18, 2008.

Applicant, Amendment After Notice of Allowance Under 37 C.F.R. 1.312, Sep. 16, 2008.

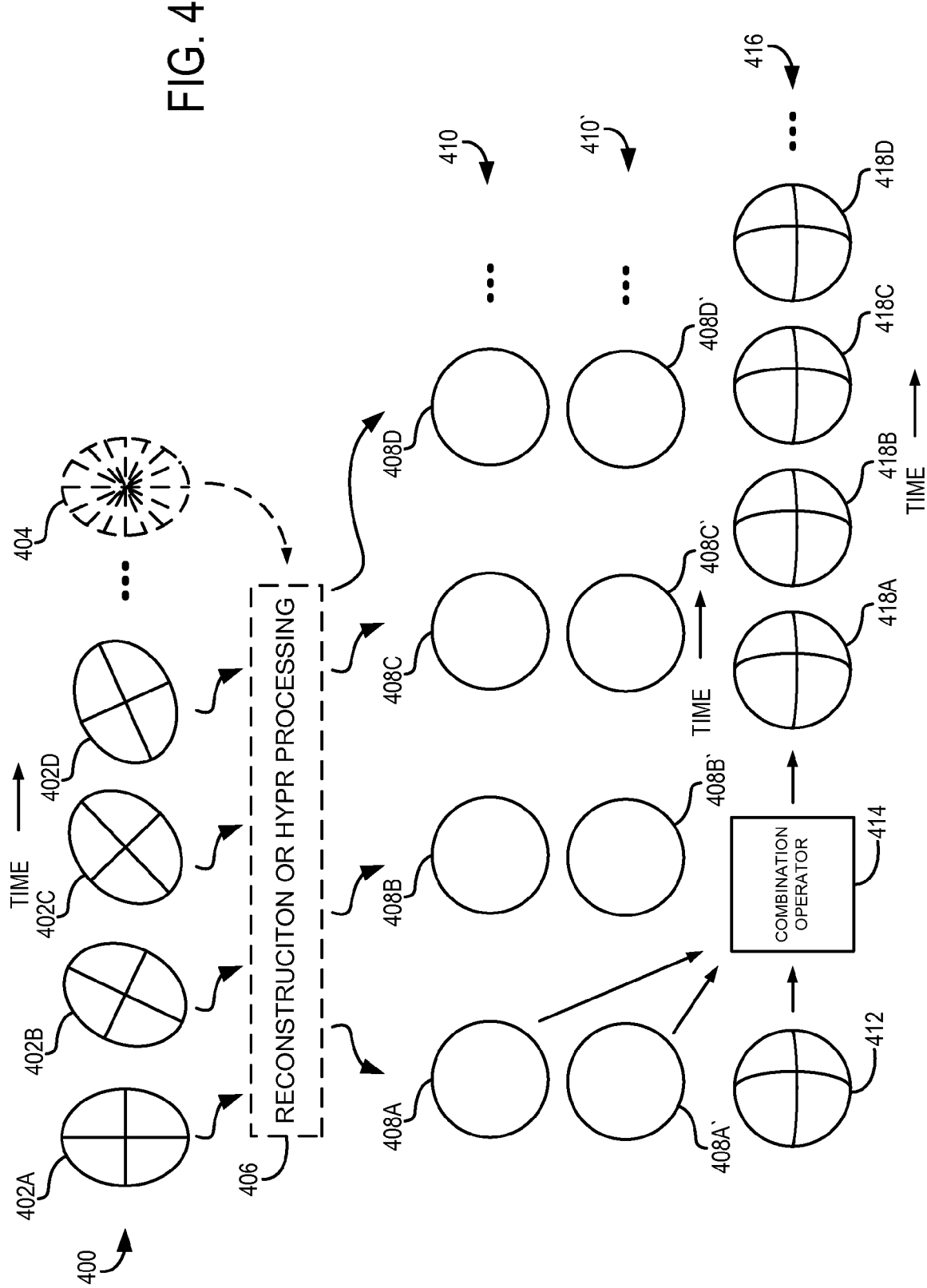

SYSTEM AND METHOD OF HIGH-FRAME RATE, TIME-RESOLVED, THREE-DIMENSIONAL MAGNETIC RESONANCE ANGIOGRAPY

STATEMENT REGARDING FEDERALLY SPONSORED RESEARCH

This invention was made with government support under NS066982 awarded by the National Institutes of Health. The government has certain rights in the invention.

BACKGROUND OF THE INVENTION

The present invention is related to angiography and, in particular, the invention relates to a system and method for producing time-resolved, three-dimensional (3D) angiographic images.

Since the introduction of angiography beginning with the direct carotid artery punctures of Moniz in 1927, there have been ongoing attempts to develop angiographic techniques that provide diagnostic images of the vasculature, while simultaneously reducing the invasiveness associated with the procedure. For decades, post-processing of images was largely limited to the use of film subtraction techniques. Initial angiographic techniques involved direct arterial punctures and the manipulation of a needle through which a contrast medium was injected. These practices were associated with a significant incidence of serious complications. The development of percutaneous techniques allowing the use of a single catheter to study multiple arterial segments reduced, but this by no means eliminated, these adverse events. In the late 1970's, a technique known as digital subtraction angiography (DSA) was developed based on real-time digital processing equipment. Because of the advantages of digital processing, it was originally hoped that DSA could be consistently implemented using an IV injection of contrast medium, thus reducing both the discomfort and the incidence of complications associated with direct IA injections.

However, it quickly became apparent that the IV-DSA technique was limited by problems due to suboptimal viewing angles and vessel overlap that could only be reduced by repeated injections. Even then, these factors were problematic unless a projection that avoided the overlap of relevant vascular structures could be defined. Similar problems occurred when using biplane acquisitions. Also, because of the limited amount of signal associated with the IV injection of contrast medium, IV-DSA was best performed in conditions with adequate cardiac output and minimal patient motion. IV-DSA was consequently replaced by techniques that combined similar digital processing with standard IA angiographic examinations. Nevertheless, because DSA can significantly reduce both the time necessary to perform an angiographic examination and the amount of contrast medium that was required, its availability resulted in a significant reduction in the adverse events associated with angiography. Due to steady advancements in both hardware and software, DSA can now provide exquisite depictions of the vasculature in both 2D and rotational 3D formats. Three-dimensional digital subtraction angiography (3D-DSA) has become an important component in the diagnosis and management of people with a large variety of central nervous system vascular diseases.

Current limitations in the temporal resolution capabilities of x-ray angiographic equipment require that rotational acquisitions be obtained over a minimum time of about 5 seconds. Even with perfect timing of an acquisition so that arterial structures are fully opacified at the onset of a rotation, there is almost always some filling of venous structures by the end of the rotation. Display of a "pure" image of arterial anatomy is only achieved by thresholding such that venous structures, which contain lower concentrations of contrast medium than arterial structures, are no longer apparent in the image. This limitation is a significant factor in making it prohibitively difficult to accurately measure the dimensions of both normal and abnormal vascular structures. Current DSA-based techniques do not depict the temporal sequence of filling in a reconstructed 3D-DSA volume.

In recent years, competition for traditional DSA has emerged in the form of CT angiography (CTA). Like traditional DSA, CTA relies upon ionizing radiation and, thus, presents a substantial drawback of requiring the subject to receive a dose of the ionizing radiation in order to acquire the desired images. Furthermore, while CTA provides high spatial resolution, it is not time-resolved unless the imaging volume is severely limited. CTA is also limited as a standalone diagnostic modality by artifacts caused by bone at the skull base and the contamination of arterial images with opacified venous structures. Further, CTA provides no functionality for guiding or monitoring minimally-invasive endovascular interventions.

Recently, improvements in DSA have been made that overcome many of the drawbacks presented by traditional DSA and newer imaging techniques, like CTA. Specifically, a technique referred to as 4D DSA has been developed for generating detailed series of time-resolved, three-dimensional medical images of a subject, with both high temporal resolution and excellent spatial resolution, by imparting temporal information from a time-series of 2D images into a still 3D image. To achieve this, 4D DSA techniques acquire a time-series of 2D-DSA images using a fluoroscopy system and acquire a 3D image substantially without temporal resolution using a the same or a different fluoroscopy or CT system. For example, in some cases, these two data sets may be acquired using a common acquisition performed, for example, using a C-arm CT system or may combine a C-arm or gantry-based CT system with a biplane fluoroscopy system to complete the acquisitions. A time-resolved, 3D image is produced by selectively combining the 3D image without temporal resolution and the time-series of 2D images. While such 4D DSA systems and methods improve upon traditional DSA or CTA capabilities, they require the use of ionizing radiation.

It would therefore be desirable to have a system and method for providing a time-resolved 3D image that is capable of providing the clinically-desirable information provided by DSA, 4D DSA, and CTA, but without the expense and complexity of combining multiple imaging sub-systems or the use of ionizing radiation.

SUMMARY OF THE INVENTION

The present invention overcomes the aforementioned drawbacks by providing a system and method for producing time-resolved 3D medical images of a subject from a time series of two-dimensional (2D) data sets and a time-independent, 3D volume of the subject. The 2D time series of images of the subject is combined with the time-independent 3D volume of the subject to generate a set of time-dependent 3D volume images of the subject at the frame rate of the acquired 2D data sets.

In accordance with one aspect of the invention, a magnetic resonance imaging (MRI) system is disclosed that includes a magnet system configured to generate a polarizing magnetic field about at least a portion of a subject arranged in the MRI system, a plurality of gradient coils configured to apply a gradient field to the polarizing magnetic field along each of at least three directions, and a radio frequency (RF) system configured to apply an excitation field to the subject and acquire MR image data therefrom. The system also includes a computer system programmed to acquire a time series of two-dimensional (2D) data sets from a portion of the subject using the plurality of gradient coils and RF system and reconstruct the time series of 2D data sets into a 2D time series of images having a given frame rate. The computer system is further programmed to acquire a time-independent, 3D volume of at least the portion of the subject and generate a set of time-dependent 3D volume images of the portion of the subject at the given frame rate using the 2D time series of images of the subject and the time-independent 3D volume of the subject.

In accordance with another aspect of the invention, a method for producing time-resolved, three-dimensional (3D) volume of a subject is disclosed that includes acquiring a time series of two-dimensional (2D) data sets from a portion of the subject using a magnetic resonance imaging (MRI) system and reconstructing the time series of 2D data sets into a 2D time series of images of the subject having a given frame rate. The method also includes acquiring a time-independent, 3D volume of the portion of the subject and combining the 2D time series of images of the subject with the time-independent 3D volume of the subject to generate a set of time-dependent 3D volume images of the portion of the subject at the given frame rate.

Various other features of the present invention will be made apparent from the following detailed description and the drawings.

BRIEF DESCRIPTION OF THE DRAWINGS

FIG. 4 is a graphic diagram illustrating a data acquisition and image reconstruction/processing process for generating ultra-high frame-rate MR imaging in accordance with the present invention.

DETAILED DESCRIPTION OF THE INVENTION

Figure 1:
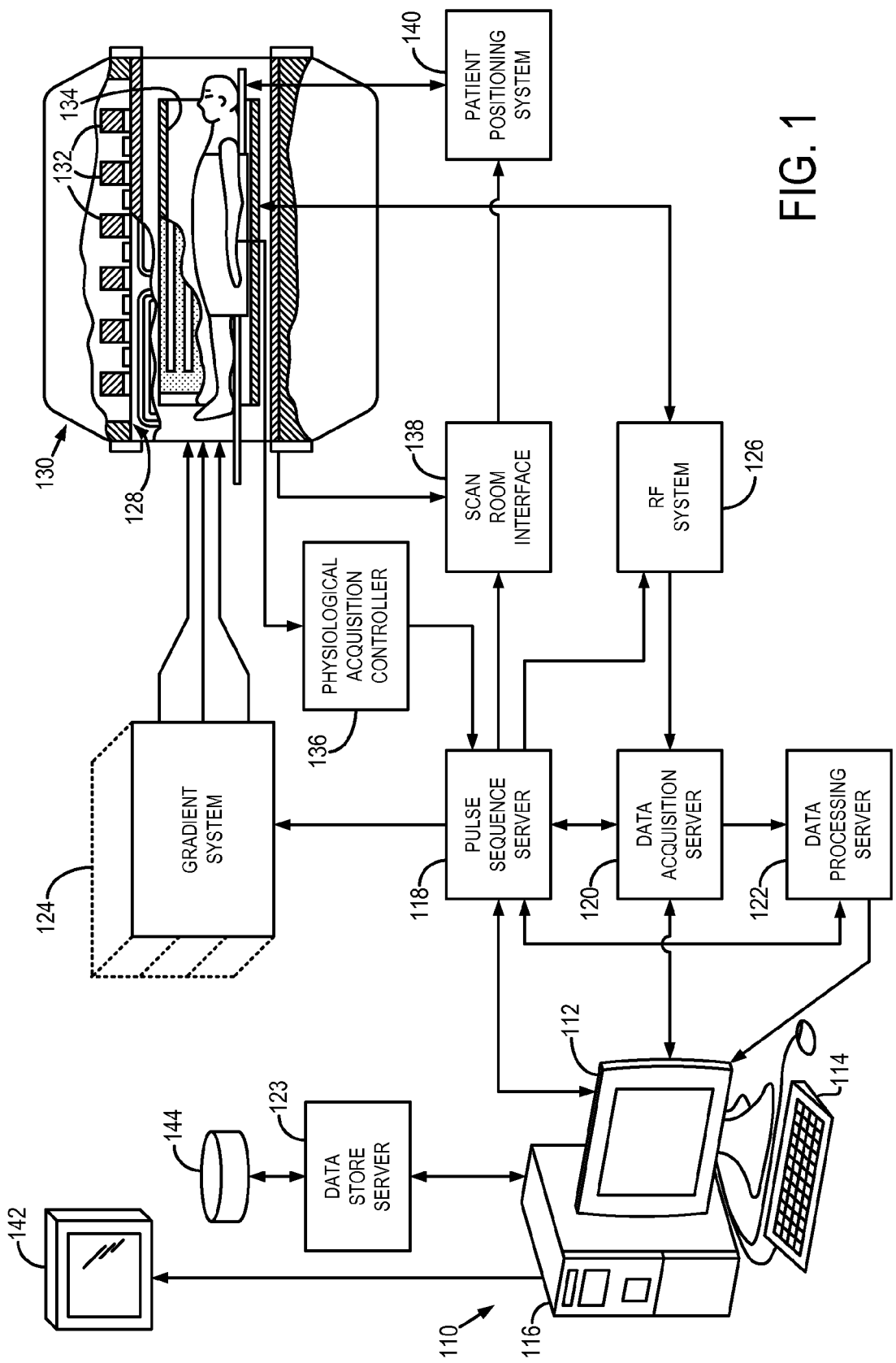
FIG. 1 is a block diagram of an MRI system for use with the present invention.

Referring to FIG. 1, the present invention is employed in an MRI system. The MRI system includes a workstation 110 having a display 112 and a keyboard 114. The workstation 110 includes a processor 116 that is a commercially available programmable machine running a commercially available operating system. The workstation 110 provides the operator interface that enables scan prescriptions to be entered into the MRI system.

The workstation 110 is coupled to, for example, four servers, including a pulse sequence server 118, a data acquisition server 120, a data processing server 122, and a data store server 123. In one configuration, the data store server 123 is performed by the workstation processor 116 and associated disc drive interface circuitry and the remaining three servers 118, 120, 122 are performed by separate processors mounted in a single enclosure and interconnected using a backplane bus. The pulse sequence server 118 employs a commercially available microprocessor and a commercially available communication controller. The data acquisition server 120 and data processing server 122 both employ commercially available microprocessors and the data processing server 122 further includes one or more array processors based on commercially available processors.

The workstation 110 and each processor for the servers 118, 120, 122 are connected to a communications network. This network conveys data that is downloaded to the servers 118, 120, 122 from the workstation 110 and conveys data that is communicated between the servers 118, 120, 122 and between the workstation 110 and the servers 118, 120, 122. In addition, a high speed data link is typically provided between the data processing server 122 and the workstation 110 in order to convey image data to the data store server 123.

The pulse sequence server 118 functions in response to program elements downloaded from the workstation 110 to operate a gradient system 124 and an RF system 126. Gradient waveforms necessary to perform the prescribed scan are produced and applied to the gradient system 124 that excites gradient coils in an assembly 128 to produce the magnetic field gradients $G_x$, $G_y$, and $G_z$ used for position encoding NMR signals. The gradient coil assembly 128 forms part of a magnet assembly 130, which includes a polarizing magnet 132 and a whole-body RF coil 34.

The RF excitation waveforms are applied to the RF coil 134 by the RF system 126 to perform the prescribed magnetic resonance pulse sequence. Responsive NMR signals detected by the RF coil 134 are received by the RF system 126, amplified, demodulated, filtered, and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 18 to produce RF pulses of the desired frequency, phase, and pulse amplitude waveform. The generated RF pulses may be applied to the whole body RF coil 134 or to one or more local coils or coil arrays.

The RF system 126 also includes one or more RF receiver channels. Each RF receiver channel includes an RF amplifier that amplifies the NMR signal received by the coil to which it is connected and a quadrature detector that detects and digitizes the in-phase (I) and quadrature (Q) components of the received NMR signal. The magnitude of the received NMR signal may thus be determined at any sampled point by the square root of the sum of the squares of the I and Q components.

The pulse sequence server 118 also optionally receives patient data from a physiological acquisition controller 136. The controller 136 receives signals from a number of different sensors connected to the patient, such as ECG signals from electrodes or respiratory signals from a bellows.

The pulse sequence server 118 also connects to a scan room interface circuit 138 that receives signals from various sensors associated with the condition of the patient and the magnet system. It is also through the scan room interface circuit 138 that a patient positioning system 140 receives commands to move the patient to desired positions during the scan.

It should be apparent that the pulse sequence server 118 performs real-time control of MRI system elements during a scan. As a result, it is necessary that its hardware elements be operated with program instructions that are executed in a timely manner by run-time programs. The description components for a scan prescription are downloaded from the workstation 110 in the form of objects. The pulse sequence server 118 contains programs that receive these objects and converts them to objects that are employed by the run-time programs.

The digitized NMR signal samples produced by the RF system 126 are received by the data acquisition server 120. The data acquisition server 120 operates in response to description components downloaded from the workstation 110 to receive the real-time NMR data and provide buffer storage such that no data is lost by data overrun. In some scans, the data acquisition server 120 does little more than pass the acquired NMR data to the data processor server 122. However, in scans that require information derived from acquired NMR data to control the further performance of the scan, the data acquisition server 120 is programmed to produce such information and convey it to the pulse sequence server 118. For example, during prescans NMR data is acquired and used to calibrate the pulse sequence performed by the pulse sequence server 118. Also, navigator signals may be acquired during a scan and used to adjust RF or gradient system operating parameters or to control the view order in which k-space is sampled.

The data processing server 122 receives NMR data from the data acquisition server 120 and processes it in accordance with description components downloaded from the workstation 110. Such processing may include, for example, Fourier transformation of raw k-space NMR data to produce two or three-dimensional images, the application of filters to a reconstructed image, the performance of a backprojection image reconstruction of acquired NMR data, the calculation of functional MR images, the calculation of motion or flow images, and the like.

Images reconstructed by the data processing server 122 are conveyed back to the workstation 110 where they are stored. Real-time images are stored in a data base memory cache (not shown) from which they may be output to operator display 112 or a display 142 that is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

Figure 2:
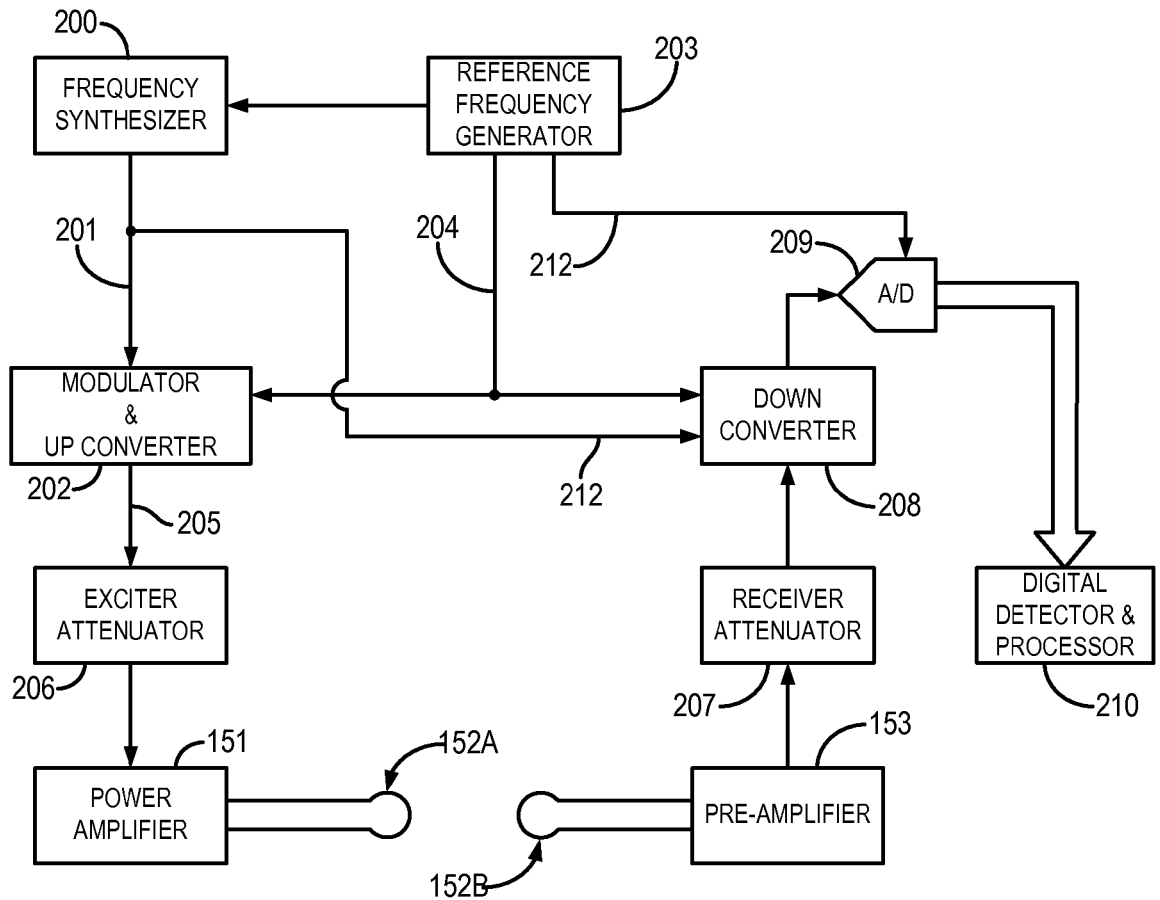
FIG. 2 is a schematic representation of a transceiver system for use with the MRI system of FIG. 1.

As shown in FIG. 1, the RF system 126 may be connected to the whole body RF coil 134, or as shown in FIG. 2, a transmitter section of the RF system 126 may connect to one RF coil 151A and its receiver section may connect to a separate RF receive coil 151B. Often, the transmitter section is connected to the whole body RF coil 34 and each receiver section is connected to a separate local coil 151B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 151A.

Referring still to FIG. 2, the signal produced by the subject is received by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two step process by a down converter 208 that first mixes the NMR signal with the carrier signal on line 201 and then mixes the resulting difference signal with a reference signal on line 204. The down converted NMR signal is applied to the input of an analog-to-digital (ND) converter 209 that samples and digitizes the analog signal and applies it to a digital detector and signal processor 210 to produce the I values and Q values corresponding to the received signal. As described above, the resulting stream of digitized I and Q values of the received signal are output to the data acquisition server 120 of FIG. 1. The reference signal, as well as the sampling signal applied to the A/D converter 209, is produced by a reference frequency generator 203.

As will be described, using the above-described MRI system and the methodology and techniques following hereafter, it is possible to provide a high frame-rate, time-series of MR images, such as is clinically desirable for performing 3D MR angiography. As will be described, the method involves the acquisition of a 2D time-series of images and a subsequent conversion to a 3D time-series of images using a separately-acquired, high-resolution, time-independent MR angiographic volume as a reconstruction constraint.

Figure 3:
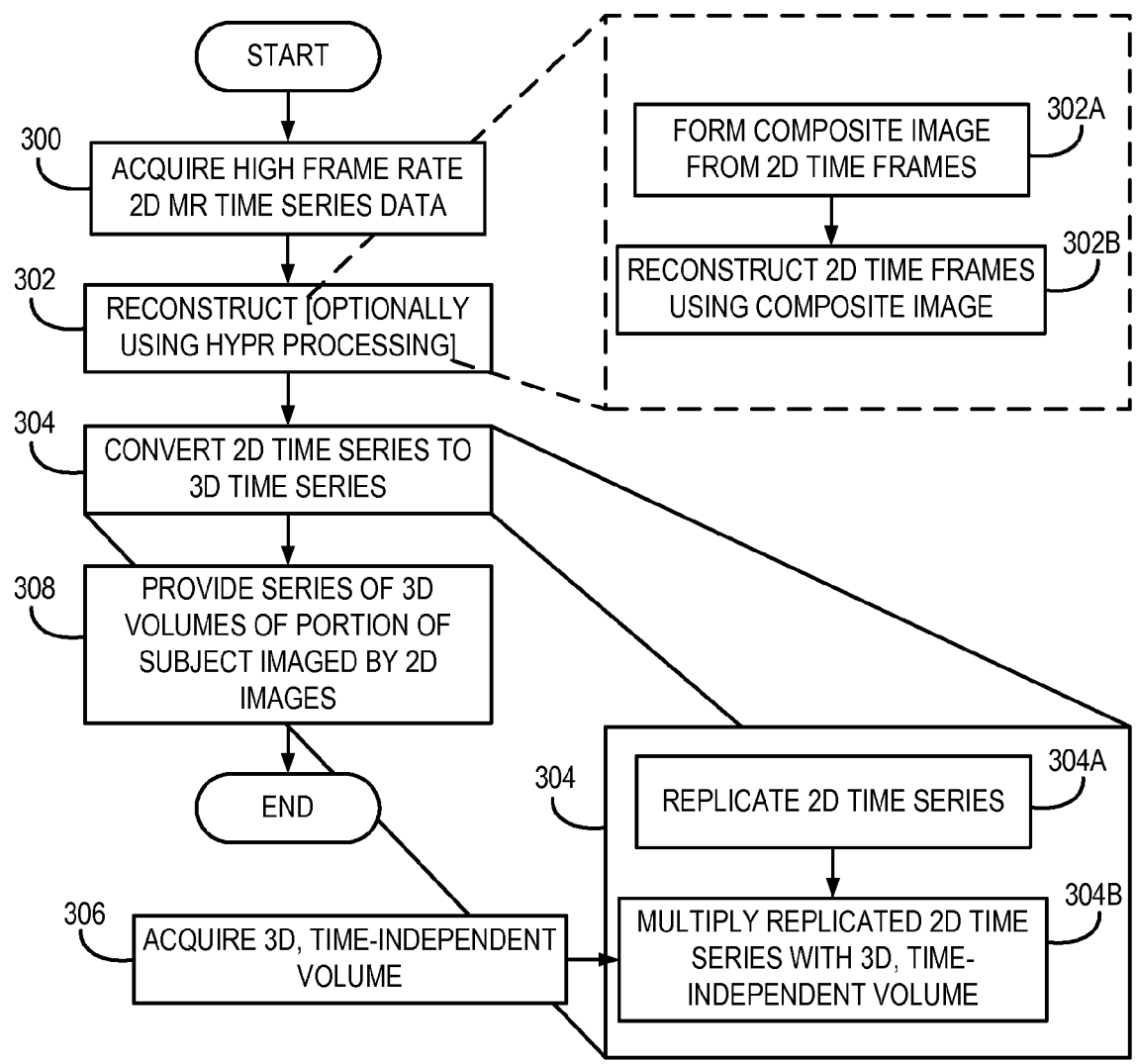
FIG. 3 is a flow chart setting forth the steps of a method for ultra-high frame-rate MR imaging in accordance with the present invention.

Referring to FIG. 3, a flow chart illustrates the steps of a method for acquiring and reconstructing ultra-high frame-rate 4D MRA images. For additional clarity, FIG. 3 will be described in conjunction with FIG. 4, which is a graphic illustration of the data acquisition and processing steps in the flow chart of FIG. 3. The process starts at process block 300 with the acquisition of time series of 2D MR images at a high frame rate. As illustrated in FIG. 4, the time-series of 2D images 400 may be acquired as interleaved projections in k-space to form a time series 402A, 402B, 402C, 402D. The acquisition of the time-series 402A, 402B, 402C, 402D can be achieved using a variety of fast MR acquisition methods, such as undersampled 2D projection imaging, echo planar imaging, and the like to acquire images having an associated high frame rate of, for example, 10-30 frames per second (fps). Within the clinical application of acquiring angiographic images, an angiographic contrast mechanism is utilized. However, the present invention is not dependent upon a particular contrast mechanism, but is advantageously amenable to any of a wide variety of contrast mechanisms including phase contrast, time of flight (TOF), traditional and variations on spin labeling (such as pulsed- or pseudo-continuous arterial spin labeling (PCASL)), contrast enhancement using an injected contrast agent, using an injected contrast agent and the like. To improve the quality of angiographic images reconstructed from the time-series data 402A, 402B, 402C, 402D, a flow dephaser may be used along the direction perpendicular to the plane in which the radial or other acquisitions are done, that is, the flow dephaser may be directed along the through-plane direction. In this regard, the flow dephaser is not coupled to the flow direction which can be arbitrary and variable within the same FOV.

At process block 302, it is contemplated that the SNR of the 2D time series data 402A, 402B, 402C, 402D acquired at process block 300 can be directly reconstructed or be optionally enhanced, for example, using a method such as the HighlY constrained PRojection (HYPR) imaging technique. To this end, U.S. Pat. No. 7,519,412 entitled "HIGHLY CONSTRAINED IMAGE RECONSTRUCTION METHOD" and U.S. Pat. No. 7,917,189 entitled "BACKPROJECTION RECONSTRUCTION METHOD FOR UNDERSAMPLED MR IMAGING" and U.S. Patent Application Publication No. 2008/0219535 and entitled "Localized and Highly Constrained Image Reconstruction Method," which describe fundamental HYPR techniques and the application of these techniques to MRI processing, are incorporated herein by reference. Furthermore, U.S. Patent Application Publication No. 2010/0286504, and entitled "CONTRAST ENHANCED MRA WITH HIGHLY CONSTRAINED BACKPROJECTION RECONSTRUCTION USING PHASE CONTRAST COMPOSITE IMAGE," describes some particular applications of HYPR techniques as applied to angiographic imaging and is also incorporated herein by reference.

Using the optional HYPR techniques, at process block 302A, a composite image 404 is formed from all or a selected group of the 2D time frames 402A, 402B, 402C, 402D. At process block 302B, the composite image is used in concert with the obtained 2D time series data in a HYPR reconstruction process 406 to reconstruct images 408A, 408B, 408C, 408D. However, it is noted that normalization, such as may be employed in traditional HYPR-based processing, may not be needed within this context. As will be described, a convolution in conjunction with converting the acquired 2D time series of images 402A, 402B, 402C, 402D into a time series of 3D volume images is used to control noise. Specifically, in HYPR-based processing there is a need to resample the composite image using a radon transformation to provide another set of projections and divide by an image that is reconstructed using the same angles as those used in the selected time frame. This step provides a quantitative normalization and may be foregone is some situations, such as when producing an angiogram. However, the convolution of the numerator image in the HYPR-based processing is still useful to achieve noise reduction.

Using HYPR, the reconstructed images will have an SNR that is significantly enhanced by the HYPR processing using the composite image 404. It is noted, however, that the present invention does not necessarily require HYPR processing or another SNR enhancing method and, thus, the HYPR processing may simply be a reconstruction process 406. Furthermore, it is noted that other SNR enhancing methods may be utilized in accordance with the present invention.

Regardless of the specific reconstruction process used or whether any SNR enhancing methods are utilized, two series of 2D images having two different view angles 410, 410' are generated to form a 2D time series of images 408A, 408B, 408C, 408D and 408A', 408B', 408C', 408D'. That is, a first time series of 2D images at a first view angle 410 is produced that is formed of a temporal series of images 408A, 408B, 408C, 408D at the first angle. Also, a second time series of 2D images at a second view angle 410' is produced that is formed of a temporal series of images 408A', 408B', 408C', 408D' at the second angle. It is noted that these view angles may be selected to be substantially arbitrary. For example, one may select angles having a difference 90 degrees or less. However, it is noted that it is generally preferably that the angles have at least a 10 to 15 degree separation.

Once the 2D MR time series data 402A, 402B, 402C, 402D has been reconstructed into two 2D time series of images 410, 410', at process block 304, the 2D time series is converted to a "quasi-3D" time series. This may be achieved using a multiplicative constrained reconstruction in which the 2D time series of images 410, 410' is converted to a 3D time series at process block 304 with identical signal in all planes perpendicular to the original 2D images. This may be accomplished, for example, using a replication function.

Specifically, referring to the conversion of the 2D time series of images 410, 410' into a "quasi-3D" time series of images at process block 304, each set of views 408A, 408A'; 408B, 408B'; 408C, 408C'; and 408D, 408D', in the series of 2D images 410, 410' is replicated at process block 304A, and combined, as indicated at 414, with a time-independent volume 412. However, before combination with the time-independent volume 412, a convolution of the 2D time series may be performed.

At process block 306A, 3D, time-independent, volume 412 of the subject are acquired. In most instances, it is desirable to acquire the 3D time-independent data from the subject contemporaneously with the acquisition of the high frame rate 2D time series data 400 acquired at process block 300. Preferably, the 3D, time-independent data accessed as volume 412 were acquired with a substantially high SNR. However, the acquisition of the set of 3D, time-independent, data at process block 306 need not directly precede or follow the acquisition of the high frame rate 2D time series data 400 acquired at process block 300. In fact, the high frame rate 2D time series data 400 may be acquired in an acquisition substantially unrelated to the acquisition of the high frame rate 2D time series data 400 acquired at process block 300 as long as the volumes can be sufficiently registered. Accordingly, process block 306 of FIG. 3 is illustrated separately from the remainder of the process blocks and the acquisition of the 3D time-independent data is not illustrated in FIG. 4. Rather, FIG. 4 illustrates the procurement of the 3D time-independent volume 412, for use as will be described.

The replicated 2D time-dependent volumes are multiplied, at process block 304B, by the separately-acquired high SNR 3D time-independent volume 412. The replicated 2D-to-3D volumes select which voxels of the separate 3D time-independent volume 412 are present at each point in time and, at process block 308, yields a series 416 of 3D volumes 418A, 4188, 418C, 418D.

Specifically, it is contemplated that the process may be achieved by at least two exemplary methodologies. First, it may be performed by first multiplying a replicated series 410 with the 3D time-independent volume 412. The square root of this product is then taken and stored, for example, as product1. This process is repeated using the second replicated series 410' to produce product2. Thereafter, the final image may be formed as the square root of the product of product1 and product2. It is noted that strategically performing this multiplication can aid in resolving ambiguities due to vessel overlap. As indicated by the shared elemental notation, the resulting series 416 of 3D volumes 418A, 418B, 418C, 418D has the frame rate of the 2D time series of data 402A, 402B, 402C, 402D and images 408A, 408B, 408C, 408D and 408A', 408B', 408C', 408D'. Second, instead of taking the square root of the product to build a given voxel, the minimum value between the two potential values for the voxel may be selected.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A magnetic resonance imaging (MRI) system comprising:
   a magnet system configured to generate a polarizing magnetic field about at least a portion of a subject arranged in the MRI system;
   a plurality of gradient coils configured to apply a gradient field to the polarizing magnetic field along each of at least three directions;
   a radio frequency (RF) system configured to apply an excitation field to the subject and acquire MR image data therefrom;
   a computer system programmed to:
      acquire a time series of two-dimensional (2D) data sets from a portion of the subject using the plurality of gradient coils and RF system;
      reconstruct the time series of 2D data sets into a 2D time series of images having a given frame rate;
      acquire a time-independent, 3D volume of at least the portion of the subject; and
      replicate the 2D time series of images to form 3D image frames; and
      multiply the 3D image frames by the time-independent 3D volume of the subject to generate a set of time-dependent 3D volume images of the portion of the subject at the given frame rate.

2. The MRI system of claim 1 wherein the computer system is further programmed to reconstruct multiple sets of 2D time series of images at different view angles when reconstructing the 2D time series of images.

3. The MRI system of claim 2 wherein the computer is programmed to multiply each view angle of the 2D time series of images separately by the time-independent 3D volume of the subject to generate the set of time-dependent 3D volume images of the portion of the subject at the given frame rate.

4. The MRI system of claim 1 wherein the computer system is further programmed to perform a HYPR-based processing technique to reconstruct the 2D time series of images.

5. The MRI system of claim 1 wherein the computer system is further programmed to acquire the time-independent, 3D volume of the portion of the subject independently from acquiring the time series of 2D data sets.

6. The MRI system of claim 1 wherein the computer system is further programmed to convolve the replicated 2D time series of images.

7. A method for producing time-resolved, three-dimensional (3D) volume of a subject, the method comprising the steps of:
   a) acquiring a time series of two-dimensional (2D) data sets from a portion of the subject using a magnetic resonance imaging (MRI) system;
   b) reconstructing the time series of 2D data sets into a 2D time series of images of the subject having a given frame rate;
   c) acquiring a time-independent, 3D volume of the portion of the subject; and
   d)i) replicating the 2D time series of images to form 3D image frames; and
   d)ii) multiplying the 3D image frames by the time-independent 3D volume of the subject to generate a set of time-dependent 3D volume images of the portion of the subject at the given frame rate.

8. The method of claim 7 wherein step b) includes reconstructing multiple sets of 2D time series of images.

9. The method of claim 8 wherein the multiple sets of 2D time series of images are at different view angles.

10. The method of claim 7 wherein step a) includes acquiring the time series 2D data sets using an interleaved radial k-space sampling.

11. The method of claim 7 wherein step b) includes performing a signal-to-noise ratio (SNR) enhancing process.

12. The method of claim 11 wherein the SNR enhancing process includes a HYPR-based processing technique.

13. The method of claim 7 wherein step c) includes acquiring the time-independent, 3D volume of the portion of the subject independently from step a).

14. The method of claim 7 wherein step d)i) includes convolving the replicated 2D time series of images.

15. The method of claim 7 wherein step d) further includes selecting a minimum value for each voxel to generate the set of time-dependent 3D volume images.

16. The method of claim 7 wherein step c) includes acquiring at least one of a phase contrast angiogram, a time-of-flight (TOF) angiogram, a spin labeled angiogram, and a contrast enhanced angiogram.

17. A method for producing time-resolved, three-dimensional (3D) volume of a subject, the method comprising the steps of:
   a) acquiring a time series of two-dimensional (2D) data sets from a portion of the subject using a magnetic resonance imaging (MRI) system;
   b) reconstructing the time series of 2D data sets into multiple sets of 2D time series of images of the subject having a given frame rate, wherein the multiple sets of 2D time series of images are at different view angles;
   c) acquiring a time-independent, 3D volume of the portion of the subject; and
   d) multiplying each view angle of the 2D time series of images separately by the time-independent 3D volume of the subject to generate a set of time-dependent 3D volume images of the portion of the subject at the given frame rate.

18. The method of claim 17 wherein step d) further includes determining a square root of a product of each multiplication.

19. The method of claim 17 wherein step d) further includes:
   d)i) replicating the 2D time series of images to form quasi-3D image frames; and
   d)ii) multiplying the quasi-3D image frames by time-independent 3D volume of the subject to generate a set of products;
   d)iii) determining a square root of a product of the set of products.

* * * * *